United States Patent [19]

Matkovich et al.

[11] Patent Number: 5,265,770
[45] Date of Patent: * Nov. 30, 1993

[54] CONTAMINATION-RESISTANT DISPENSING AND METERING DEVICE

[75] Inventors: Vlado I. Matkovich, Glen Cove; Thomas J. Bormann, Seaford, both of N.Y.

[73] Assignees: Pall Corporation, Glen Cove, N.Y.; Merck and Company, Rahway, N.J.

[*] Notice: The portion of the term of this patent subsequent to Jun. 15, 2010 has been disclaimed.

[21] Appl. No.: 882,755

[22] Filed: May 11, 1992

Related U.S. Application Data

[63] Continuation of Ser. No. 531,243, May 31, 1990, abandoned, which is a continuation-in-part of Ser. No. 360,041, Jun. 1, 1989, abandoned.

[51] Int. Cl.$^5$ .................... B67D 5/58; B65D 47/18
[52] U.S. Cl. ........................ 222/189; 222/212; 222/420; 222/568; 210/321.64; 210/321.84; 210/500.38; 210/500.42; 604/298
[58] Field of Search ............... 222/189, 190, 206, 212, 222/215, 420, 421, 562, 566, 567, 568, 570, 571, 575; 210/321.64, 321.84, 490, 500.38, 500.42; 604/126, 294, 295, 298, 300-302

[56] References Cited

U.S. PATENT DOCUMENTS

| | | | |
|---|---|---|---|
| 2,263,890 | 11/1941 | Salvesen | 215/74 |
| 2,757,824 | 8/1956 | Savary | 222/566 X |
| 2,806,637 | 9/1957 | Wallingford | 222/215 |
| 2,987,223 | 6/1961 | Armour | |
| 3,149,758 | 9/1964 | Bush et al. | 222/189 |
| 3,189,223 | 6/1965 | Mackal | |
| 3,241,731 | 3/1966 | Bright et al. | 222/568 |
| 3,248,017 | 4/1966 | Allen | |
| 3,449,081 | 6/1969 | Hughes | |
| 3,631,654 | 1/1972 | Riely et al. | |
| 3,645,262 | 2/1972 | Harrigan | 222/570 X |
| 3,760,987 | 9/1973 | Meterhoefer | |
| 4,002,168 | 1/1977 | Petterson | 222/421 X |
| 4,093,124 | 6/1978 | Morane et al. | |
| 4,203,848 | 5/1980 | Grandine, II | 210/490 |
| 4,319,996 | 3/1982 | Vincent et al. | |
| 4,401,270 | 8/1983 | McKinney | 222/215 X |
| 4,463,880 | 8/1984 | Kramer et al. | 222/420 X |
| 4,471,890 | 9/1984 | Dougherty | |
| 4,533,068 | 8/1985 | Meierhoefer | 222/189 |
| 4,797,259 | 1/1989 | Matkovich et al. | |
| 4,915,839 | 4/1990 | Marinaccio et al. | |
| 4,917,271 | 4/1990 | Kanner et al. | 222/568 X |
| 4,938,389 | 7/1990 | Ross et al. | 222/420 X |
| 4,968,310 | 11/1990 | Menchel | 222/206 X |
| 5,040,706 | 8/1991 | Davis et al. | 222/420 X |

FOREIGN PATENT DOCUMENTS

| | | | |
|---|---|---|---|
| 82714 | 4/1957 | Denmark | 222/420 |
| 0190558 | 8/1986 | European Pat. Off. | |
| 167562 | 1/1951 | Fed. Rep. of Germany | 222/206 |
| 3628197 | 2/1988 | Fed. Rep. of Germany | |
| 1365410 | 5/1964 | France | 222/420 |
| 661203 | 3/1964 | Italy | 222/420 |
| WO88/0735 | 9/1988 | PCT Int'l Appl. | |
| 1067285 | 5/1967 | United Kingdom | |
| 2021429 | 12/1979 | United Kingdom | |
| 2132989 | 7/1984 | United Kingdom | |

Primary Examiner—Joseph E. Valenza
Assistant Examiner—Boris Milef
Attorney, Agent, or Firm—Leydig, Voit & Mayer

[57] ABSTRACT

A cap for dispensing liquids from a container comprising a base portion; structure to attach the base portion to a container; and an off-center dispenser tip projecting from the base portion and having a passageway extending between an orifice at the distal end of the dispenser tip and the interior underside of the cap, the axis of said passageway forming an angle of no greater than 90 with the longitudinal axis of the base. Included is a composite membrane having liquophilic and liquophobic components for preventing fluid contamination and metering dispersing.

53 Claims, 6 Drawing Sheets

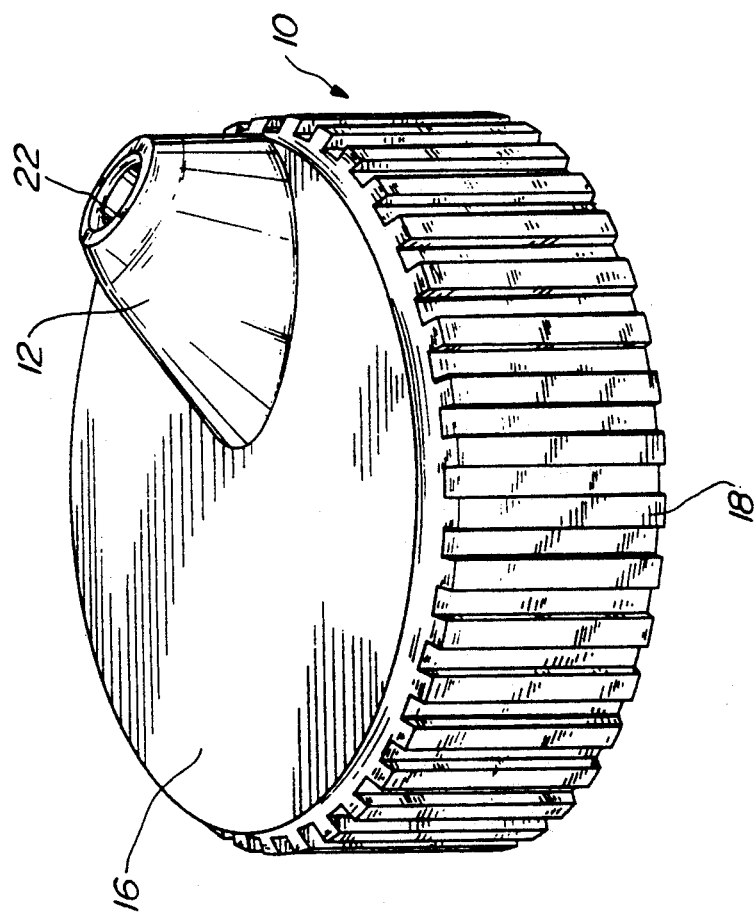

5,265,770

CONTAMINATION-RESISTANT DISPENSING AND METERING DEVICE

This application is a continuation of application Ser. No. 07/531,243, filed May 31, 1990, now abandoned, which is a continuation-in-part of application Ser. No. 07/360,041, filed Jun. 1, 1989 now abandoned.

TECHNICAL FIELD

This invention relates to a liquid dispensing and metering device that is especially useful in, for example, the dispensing of ophthalmic drugs that typically need to be dispensed in drop form. The present invention provides such a device that also protects the solution from contamination while retained in the device.

BACKGROUND OF THE INVENTION

This invention has wide application in situations where a liquid is required to be dispensed in metered amounts at regular intervals from a container and in which it is critical that contamination from outside, whether particulate or bacterial in nature, be excluded. This is most frequently encountered in the context of the dispensing of medicines such as ophthalmic medicines but the utility of the invention extends to the protection of any liquid against particulate contamination. For ease of understanding, however, the invention will be described primarily in the context of the application that, as is presently anticipated, will be the most commercially attractive.

Many drugs, particularly those used in treatment of various eye disorders, are administered in drop form. The drops are intended to free-fall onto the eye surface, where they distribute across the exposed eye. Dosage of these ophthalmic drugs is often crucial: lower than prescribed levels can result in failure of the treatment and consequent progression of the disease, higher levels can result in untoward side effects that can also interfere with successful resolution.

Complicating the administration of these drugs is the fact that they are often required several times a day and thus, to be practical, must be applied by the patients themselves and not by medical personnel who are formally trained in drug delivery. Patient administration of such drugs has resulted in two serious problems and several inconveniences, the solution of which will allow these medications to be successfully and efficiently used: container contamination and flow rate.

CONTAINER CONTAMINATION

The possibility that bacterial contamination may enter the drug container and proliferate there is an ever-present problem that can destroy the utility of the medicine. This can be the result of dropper contact with a non-sterile surface, such as a body part, or by some other mechanism.

The problem can be most readily understood in the context of the administration of drops of an ophthalmic medicine. Ideally, the pendant drop formed at the tip of the conventional dropper container when the container is squeezed should be allowed to free-fall to the surface of the eye. In addition, the distance between the dropper tip and the surface of the eye should be kept reasonably close. This is important so that the momentum acquired by the free-falling drop will not be so great as to encourage the drop to splatter on impact with the eye surface and thus be substantially lost to the outer surface of the lids and face. Where administration is by a trained professional, it is relatively easy to ensure that the free-falling drop is discharged close to the eye surface. It is substantially more difficult to do this when the drug is self-administered. Gauging such short distances is physiologically difficult due to the inability to focus, and in addition the anticipation of the impacting drop often causes a blink and subsequent loss of portions of the drop. As a result, the user may inadvertently permit the dropper tip to contact the eye surface.

In any event, small amounts of eye liquids can thus be inadvertently permitted to commingle with the liquid of the drop to be delivered. Thus, when the pressure on the delivery container forcing the drop out is relieved, a small amount of the mixed liquids may be drawn back into the container. With time the bacteria originally present in the eye, both normal and pathological, will be permitted access to a medium which may cause them to proliferate. Thus, subsequent drops of medication may reintroduce to the eye either excessive levels of typically present bacteria, or large numbers of pathogens. Neither situation is acceptable.

To cope with the problems of contamination, drug manufacturers often introduce an anti-bacterial agent to the drug container. In most cases, this agent or preservative can be very effective at sup-pressing the growth of bacterial contaminants within the container. Unfortunately, there exists a significant population of patients for whom these preservatives represent ocular irritants, or in more severe cases, cause allergic reactions. Such untoward ocular reactions prevent such patients from using the drug in this kind of packaging. For these patients, single-use, non-preserved drug packaging is a partial answer, but at significantly increased cost and inconvenience.

Of course, similar problems are encountered with other drop-administered medicines, for example, for the ear or nose.

Container contamination can also be the result of particulate matter being drawn back into the container with the liquid in the dropper tip that has not been delivered as a drop. Over several drop deliveries in, for example, dusty conditions, a significant accumulation of dust in the container is possible. If the liquid to be delivered needs to be ultrapure as, for example, in certain microelectronic applications, such accumulation could raise a serious problem.

FLOW RATE

Dosage of drugs administered as drops is regulated on the basis of the number of drops to be applied. Formation of the drops is directly related to flow rate of the liquid from the container. The drops themselves fall from the dropper tip when the weight of the pendant exceeds the surface tension forces holding the drop to the dropper tip. In the ideal case, each drop should be identical to the previous one. In practice, however, other factors intervene to cause significant variation in drop size. One of the most significant factors is the rate of drop formation. If the drop is formed rapidly, more liquid can be "injected" into the body of the drop as it is beginning to break free. These drops will be larger, and thus will carry more drug, than if the container is squeezed very slowly. In extreme circumstances, drug may be ejected in a steady stream.

While this is a minimal problem when the drugs are delivered by a trained professional, it becomes significant when the drugs are delivered by the patients themselves. The flow rate, which is directly related to the finger pressure while squeezing, cannot be easily controlled.

Facile flow control is also impeded in many liquid delivery systems or dispensers by restrictive means provided for a particular purpose, located in or proximate the tip of the dispenser. In many instances, such restrictive means requires a large pressure to initiate fluid flow from the dispenser which, at such pressures, tends to cause a rapid sequence of drops to be expelled. The visual clue, that is, the growth of the drop itself, cannot be readily observed if the eye is about to receive the same drop or if the dropper is not positioned in the line of sight in use.

In addition when using conventional liquid dispensing bottles in which a dispenser tip projects coaxially with respect to the longitudinal axis of the container and perpendicular to the face of the cap, unless the container is carefully oriented with respect to ground or the upturned user's eye, there is a significant tendency to lose or misdirect liquid. That is, when the tip of a conventional liquid dispenser is moved from a position of being oriented vertically or perpendicular to the surface of the user's eye to a position oriented horizontally or parallel to the surface of a user's eye the drop of liquid formed at the orifice of the dropper tip rather than dropping freely from the tip tends to cling to the projecting tip and roll to one side before falling from the tip. This increases the tendency to pick up contamination and uneven size drops and amount of medication reaching the eye.

The problem of delivery control is not restricted to ophthalmic drugs, of course, and there is a clear need for controllable addition devices in a wide range of, for example, pharmaceutical dispensing applications.

DESCRIPTION OF THE INVENTION

In the metering device defined in the present invention there is an inherently greater resistance to liquid flow than in a metering device of the prior art. For this reason, it becomes most difficult to produce a continuous stream of liquid by squeezing the container. This resistance to liquid flow also tends to damp out the natural variations in squeezing force that occur from moment to moment during use of a metering device of this type. As a result, the sequential drops metered from such a device tend to have a much more uniform size.

It is therefore an object of this invention to provide a flow metering device in which the problems of contamination and uncontrolled flow rate are substantially reduced.

It is a further object of this invention to provide a dropper for ocular medicines that is protected from inadvertent bacterial contamination and thus permit a significant reduction or the complete elimination of preservatives in the medicine.

It is another object of the invention to provide a liquid metering and dispensing device in which a liquid, such as a medicine, is dispensed as substantially uniform drops.

It is an additional object of this invention to provide a liquid dispenser which permits dispensing drops of uniform size and in the exact number desired.

A further object of the invention is to provide a liquid dispenser and a cap which may be used in a liquid dispenser of the type used for self administration of a liquid to the eye which is both comfortable to hold at an appropriate angle with respect to the eye and which reduces the tendency to use or misdirect drops of the liquid.

The above objects are provided by a device for dispensing a liquid in drop form which comprises a container having a dropper tip, integrally formed or in a cap attached to the container, comprising a passageway for ingress of air to and egress of liquid from the device, the passageway communicating between the body of the container and an orifice, means for temporarily reducing the volume of the container and, disposed within the dropper tip, across the passageway and adjacent the orifice, a composite microporous membrane with pores of a size to resist the passage of undesired contamination, the membrane having a liquophilic portion permitting delivery of metered drops of a liquid to a desired location outside the con-tainer, and a liquophobic portion adapted to resist the passage of such liquid but to permit the passage therethrough of air, the passageway communicating with both the liquophilic and liquophobic portions.

The membrane is sealed to the inside surface of the dropper within the tip region so as to prevent the passage of liquid around, as opposed to through, the membrane.

The membrane comprises two components in side-by-side or juxtaposed relationship. One component has a liquophobic character, that is, it resists the pas-sage of liquids. The other component has a liquophilic character, that is, liquids pass through it readily. Thus, liquids exiting the container through the porous membrane will pass exclusively through the liquophilic component and will be rejected by the liquophobic component. Liquids being sucked back into the container will pass exclusively through the liquophilic component. However, air will flow into the container to replace the expelled liquid through the liquophobic side.

THE CONTAINER

In use, the container functions as a reservoir for the liquid to be dispensed. It is provided with means to temporarily reduce its volume, typically by providing that at least part of the container is elastically deformable. Thus, pressure on a deformable portion of the container will reduce the effective volume and force the liquid contained therein out of the container when it is appropriately oriented.

After a desired number of drops have been expelled from the container and the deforming pressure is removed, the liquid below the membrane in the tip is drawn back into the container. It is preferred that this occurs as a continuous column, that is, no droplets should break away and be left behind in the tip area. Such droplets could be a hospitable environment for bacterial growth and as such should be avoided so far as possible. Making the volume of the tip area very small helps to minimize this problem. It is, therefore, particularly preferred that the volume between the orifice of the dropper and the surface of the composite membrane be as small as possible. Volumes of the order of from about 0.001 to about 0.15 cm$^3$ are suitable and most preferred are volumes of from about 0.05 to about 0.1 cm$^3$.

The tip area of the dropper can be designed to provide membrane support by various means including, for example, a series of ribs on the inside surface of the dropper tip and/or an interior beading providing a seating surface to which the membrane can be bonded. Care should, however, be exercised to ensure that such support devices do not impede or distort the flow of metered drops from the device. Support could also be provided by the provision of a transverse septum or bar that would help resist any tendency of the membrane to deform under pressure.

DISPENSER TIP AND CAP

As indicated above, the dispenser tip may be integrally formed with the container or may be provided in a cap which is attached to the container by conventional attachment means. Examples of these attachment means include commensurately configured engaging portions such as threaded portions or pin and receiving portions, on both the cap and container. Alternatively, the cap and container may be joined to one another by means of an interference (press) fitting or by welding or gluing, the latter term including the use of any type of adhesive.

In a conventional liquid dispenser, of the type used to dispense small volumes of liquid medicaments, and particularly of the type used to administer drops to the eyes, a dispenser tip is located at the center of the cap, concentric with the longitudinal axis of the cap (and/or container). While this type of dispenser tip may be satisfactory in some applications, when dispensing small uniform drops of liquid, particularly in situations in which contamination is a concern, as indicated above, it is highly desirable to keep the volume of the tip as small as possible. This assures a smaller region for breeding biological contaminants and allows easier control of fluid flow without expelling a rapid uncontrolled sequence of drops. However, when a small dispenser tip is centrally located in the cap, because of the orientation at which the average user tends to hold the device, there is some tendency to administer contaminated drops, miss the target, in some instances get nonuniform drops or lose drops altogether. This tends to occur in part because of the small size of the dispenser tip and because the most comfortable position of the hand when a small dispenser is raised above eye level to administer drops to the eye is one in which the axis of the dispenser tip approaches an orientation parallel to the eye. In this position, in contrast to the ideal position in which the dispenser tip is held perpendicular to the eye, the drops tend, as and after they form, to roll to one side along the lower outer surface of the dispenser tip. Thus, they pick up contaminants present on the external surface of the dispenser tip. Some drops roll to the side and fall from the dispenser tip missing the intended target, the eye, altogether.

When the dispenser tip is small, as when a small volume in the tip is required, contamination and loss of drops is more likely since the side of the drop tends to contact the surface of the cap adjacent the dispenser tip as the diameter of the drop swells during its formation.

The present invention overcomes such problems by locating the dispenser tip off-center, preferably proximate a side of the base and with an orientation of the tip such that the axis of the passageway forms an angle with the longitudinal axis of the cap (container) of no greater than 90°. (For purposes of the present invention, an angle of 0° exists when the dispenser tip projects directly away from the container, the axis of the dispenser tip passageway being parallel to the longitudinal axis.) Preferably the angle is about 30° to about 60°, most preferably about 40° to about 50°. It is preferred that at least one side of the dispenser tip, and preferably the side nearest the side of the cap at which the dispenser tip is located is parallel to a skirt section of the cap. It is most preferred that a portion of the surface of the dispenser tip is substantially tangent to or coextensive with a portion of the surface of a skirt portion of the cap.

It is preferred that the rim formed at the distal or remote end of the dispenser tip define a plane which forms an angle with respect to the axis of the dispenser tip passageway of 90°± about 45°. Most preferably, the plane is substantially perpendicular to the passageway axis.

WETTING OF POROUS MEDIA

The wettability or liquophilicity of a porous structure, e.g., a membrane, is a function of that structure's critical wetting surface tension (CWST) (discussed below) and the surface tension of the applied liquid. If the CWST is at least as high as the surface tension of the liquid, the liquid will spontaneously wet the porous structure, which may be termed "liquophilic" with respect to that liquid. Conversely, if the CWST is lower than the surface tension of the liquid then it will not be wet and will be liquophobic with respect to that liquid.

When a liquid is brought into contact with the upstream surface of a porous medium and a small pressure differential is applied, flow into and through the porous medium may or may not occur. A condition in which no flow occurs is that in which the liquid does not wet the material of which the porous structure is made.

A series of liquids can be prepared, each with a surface tension about 3 dynes/cm higher compared with the one preceding. A drop of each may then be placed on a porous surface and observed to determine whether it is absorbed quickly, or remains on the surface. For example, applying this technique to a 0.2 μm porous polytetrafluoroethylene (PTFE) membrane, instant wetting is observed for a liquid with a surface tension of about 26 dynes/cm. However, the structure remains unwetted when a liquid with a surface tension of about 29 dynes/cm is applied.

Similar behavior is observed for porous media made using other synthetic resins, with the wet/unwet values dependent principally on the surface characteristics of the material from which the porous medium is made and, secondarily, on the pore size characteristics of the porous medium. For example, fibrous polyester, specifically polybutylene terephthalate (hereinafter "PBT") sheets which have pore diameters less than about 20 μm will be wetted by a liquid with a surface tension of about 50 dynes/cm, but will not be wetted by a liquid with a surface tension of about 54 dynes/cm.

In order to characterize this behavior of a porous membrane, the term "critical wetting surface tension" (CWST) is defined as follows. The CWST of a porous medium may be determined by individually applying to its surface a series of liquids with surface tensions varying by about 2 to about 4 dynes/cm, and observing the absorption or non-absorption of each liquid. The CWST of a porous medium, in units of dynes/cm, is defined as the mean value of the surface tension of the liquid which is absorbed and that of a liquid of neighboring surface tension which is not absorbed. Thus, in the examples of the two preceding paragraphs, the CWST's are about 27.5 and about 52 dynes/cm, respectively.

In measuring CWST, a series of standard liquids for testing is prepared with surface tensions varying in a sequential manner by about 2 to about 4 dynes/cm. Ten drops from each of at least two of the sequential surface tension standard liquids are independently placed on representative portions of the porous medium and allowed to stand for 10 minutes. Visual observation is made after 10 minutes. Wetting is defined as absorption into the porous medium by at least nine of the ten drops within 10 minutes. Non-wetting is defined by non-absorption or non-wetting of at least nine of the ten drops in 10 minutes. Testing is continued using liquids of successively higher or lower surface tension, until a pair has been identified, one wetting and one non-wetting, which are the most closely spaced in surface tension. The CWST is then within that range and, for convenience, the average of the two surface tensions is used as a single number to specify the CWST.

A number of alternative methods for contacting porous media with liquids of sequentially varying surface tension can be expected to suggest themselves to a person knowledgeable of physical chemistry after reading the description above. One such involves floating a specimen on the surfaces of liquids of sequentially varying surface tension values, and observing for wet-through of the liquid or, if the fiber used is more dense than water, observing for sinking or floating. Another means would clamp the test specimen in a suitable jig, followed by wetting with the test liquids while applying varying degrees of vacuum to the underside of the specimen.

Appropriate solutions with varying surface tension can be prepared in a variety of ways; however, those used in the development of the product described herein were:

| Solution or fluid | Surface Tension range, dynes/cm |
|---|---|
| Sodium hydroxide in water | 94–110 |
| Calcium chloride in water | 90–94 |
| Sodium nitrate in water | 75–87 |
| Pure water | 72.4 |
| Acetic acid in water | 38–69 |
| Ethanol in water | 22–35 |
| n-Hexane | 18.4 |
| FC77 (3M Corp.) | 15 |
| FC84 (3M Corp.) | 13 |

LIQUOPHILIC MEDIUM

Suitable materials for the liquophilic medium include forms of polyamides, polyvinylidene fluoride, and cellulose compounds, such as nitrocellulose and mixed esters of cellulose, as well as glass fiber mats with suitable binders. Hydrophilic, microporous polyamide membranes, particularly nylon 66 membranes, are especially preferred.

A preferred microporous, hydrophilic nylon 66 membrane material having high binding capacity, uniformity, controlled pore size, and high surface area is Biodyne TM, available from Pall Corporation or one of the hydrophilic membranes described in U.S. Pat. No. 4,340,479.

Another preferred membrane useful as the liquophilic medium is the CARBOXYDYNE ® membrane, also available from Pall Corporation. CARBOXYDYNE ® is a hydrophilic, microporous, skinless nylon 66 membrane with controlled surface properties formed by the cocasting process described in U.S. Pat. No. 4,707,266, as discussed below, specifically by cocasting nylon 66 and a polymer containing an abundance of carboxyl groups to form a membrane having controlled surface properties characterized by carboxyl functional groups at its surface.

Polyvinylidene fluoride membranes are not inherently water-wettable but can be rendered such by an appropriate surface treatment. Microporous, polyvinylidene fluoride membranes which have been treated to render them hydrophilic are commercially available. As discussed above, wettability or liquophilicity is a function of the CWST of the porous membrane and the surface tension of the liquid. Wettability may also be expressed in terms of intrusion pressure required for liquid to penetrate into the pores of the membrane. Membrane materials which are particularly preferred have intrusion pressures of, or close to, zero for the liquids with which they are used.

These hydrophilic, microporous, substantially alcohol-insoluble polyamide membranes with controlled surface properties are formed by cocasting an alcohol-insoluble polyamide resin with a water-soluble, membrane-surface-modifying polymer having functional polar groups. Like the preferred hydrophilic, microporous nylon membranes which do not have controlled surface modified polar groups present, the polyamide membranes of the present invention having controlled surface properties are also skinless; that is, they are characterized by through pores extending from surface to surface which are of substantially uniform size and shape.

LIQUOPHOBIC MEDIUM

The term "liquophobic" as used herein is effectively the obverse of the term "liquophilic", that is, a porous liquophobic material has a CWST lower than the surface tension of the applied liquid and is not readily or spontaneously wetted by the applied liquid(s). Liquophobic materials are characterized, then, by a high contact angle between a drop of liquid placed on the surface and the surface. Such a high contact angle indicates poor wetting.

Another way of expressing the suitability of a material for use as the liquophobic component of the instant invention relates to the wetting resistance characteristics of the material. A suitable material should be capable of resisting a liquid intrusion pressure greater than the pressure that can be generated by manual squeezing of the dispensing bottle. Suitable materials include polyolefins, such as polypropylene, polyhalogenated polyolefins, particularly perfluorinated polyolefins, such as polytetrafluoroethylene, and polyvinylidene difluoride, as well as sulfones. Polytetrafluoroethylene is a preferred polymer and surface modified polyvinylidene difluoride, particularly a fluoropolymer-grafted microporous polyvinylidene difluoride membrane or similarly surface modified polyamides are most preferred. Particularly preferred is a polyamide which has been surface modified to have a CWST of less than about 29 dynes/cm.

The liquophobic component of the membrane typically has a CWST of less than about 35 dynes/cm and typically from about 20 dynes/cm to about 30 dynes/cm. By contrast, the liquophilic component of the membrane has a CWST of at least about 50 dynes/cm, such as from about 70 dynes/cm to about 100 dynes/cm, and preferably from about 72 dynes/cm to about 95 dynes/cm.

THE COMPOSITE MEMBRANE

The composite membrane used in the present invention has both a liquophilic, preferably hydrophilic component and a liquophobic, preferably hydrophobic component. Most frequently, these will be bonded together along the line of contact so as to form a single unit with the components in juxtaposed or side-by-side (as opposed to superposed or face-to-face) relationship to one another. Part of the composite will, preferably, be hydrophilic with respect to the liquid to be dispensed with the device and the other part will, preferably, be hydrophobic with respect to that same liquid. It is to be understood, however, that the term "composite membrane" is also intended to cover the functional equivalent of such a membrane where the two components are not physically joined but act to close off separate but adjacent exit passages from the device. One example would be provided by a device with a dropper tip having a transverse septum or bar in the area of the dropper tip dividing the exit passageway effectively in two. With such a device each membrane could be sealed to the septum or bar and the inside wall of the tip and there would be no need for bonding the two membranes together. Indeed, this configuration might confer useful support benefits for the membranes.

Both components of the membrane have a pore size adapted to resist passage of an undesired contaminant. Most frequently, in the medicinal context, this will be bacterial contamination. In this context, for the liquophilic component, pore sizes of from about 0.04 to about 0.65 $\mu$m are suitable. Preferred are pore sizes of from about 0.01 to about 0.45 $\mu$m and most preferred are pore sizes of from about 0.15 to about 0.2 $\mu$m. The liquophobic component, however, generally has a pore size of from about 0.01 to about 0.45 $\mu$m with from about 0.04 to about 0.2 $\mu$m preferred and from about 0.1 to about 0.2 $\mu$m most preferred. If particulate contamination is the main concern, the pore sizes can be redefined accordingly.

The liquophilic and liquophobic membranes can be attached within the dropper tip by known techniques, such as heat welding or ultrasonic welding. For proper function the formation of a bacteria-tight seal at the entire perimeter of the weld is critical. It is also necessary to form a bacteria-tight seal at the junction of the liquophilic and liquophobic membranes. This can be achieved by bonding the membranes together in a separate operation, with the minimum overlap required to assure a complete seal. Ultrasonic welding techniques are often preferred for this operation though good results can be obtained by heat sealing. Overlaps of less than or equal to about 3 mm (0.12 in) are preferred, and less than or equal to about 1 mm (0.039 in) are most preferred.

After bonding the membranes, discs of the membrane pairs may be punched out using conventional die punching techniques. The position of the die above and below the bond line can be used to set the relative proportions of the liquophilic and liquophobic areas of the membranes.

After punching, the discs may be transferred to the base of the dropper tip and welded in position. Alternatively, two separate regions of the dropper base may be defined and individual components of the liquophilic and liquophobic membranes welded thereto.

It is found that the bonding operation is often much simplified if the substrate membrane of both the liquophilic and liquophobic components is the same. This can be achieved by surface modification of chemically identical or closely related polymeric membranes to give liquophilic and liquophobic components which are then joined together to form the composite membranes useful in the device of the invention. Composite membranes in which both components are suitably surface-modified polyamides are particularly preferred.

The surface area of the composite membrane can be divided between liquophilic and liquophobic components in any convenient proportion. However, the proportions should be consistent with the functions that the components have to fulfill. The liquophilic membrane should be of such a size that the liquid within the container will be dispensed in drops at an appropriate rate. Too large an area could result in a high rate of flow or even, in extreme cases, a stream of liquid. On the other hand, too small an area would result in a very low drop delivery rate.

METERING FUNCTION OF THE HYDROPHILIC COMPONENT

An important aspect of the present invention is the provision of a deformable dropper bottle that meters out drops at a carefully regulated flow rate. When the liquophilic portion of the membrane selected is hydrophilic with respect to the liquid to be dispensed and has a porosity that is fine enough to exclude bacteria, the factor that controls the rate at which drops are dispensed is the surface area of the liquophilic, preferably hydrophilic portion of the membrane. This drop formation rate is largely independent of the pressure differentials caused by any deformations of the dropper bottle likely to be encountered in the normal use of such devices. This is, of course, a significant safety factor since the dropper bottle, by design and intent, will be for use by medically untrained people with varying interpretations of the level of pressure needed to express one drop from the bottle.

The hydrophilic membrane surface area that is best suited to produce an appropriate liquid flow rate in the above circumstances is found to be from about 20 mm$^2$ to about 90 mm$^2$, and preferably from about 40 mm$^2$ to about 50 mm$^2$.

The liquophobic, preferably hydrophobic, component should be large enough to accommodate relatively easy but controlled access of air to replace the liquid dispensed. It is found that, with devices of the size normally employed for eye droppers, satisfactory results may be obtained when the proportion of the liquophilic component is from about 50 to about 70% of the total surface area of the composite membrane. This provides sufficient surface area of the liquophilic, preferably hydrophilic, component to ensure a satisfactory flow rate from the dropper bottle when it is deformed. Particularly preferred, however, are membranes where about 60 to about 70% of the surface area is provided by the liquophilic component. It is recognized, how-ever, that some applications may require proportions outside the above ranges.

DESCRIPTION OF THE DRAWINGS

FIG. 6 is a perspective view illustrating ornamental features of the dispensing cap according to the present invention.

DESCRIPTION OF PREFERRED EMBODIMENTS

Figure 1:
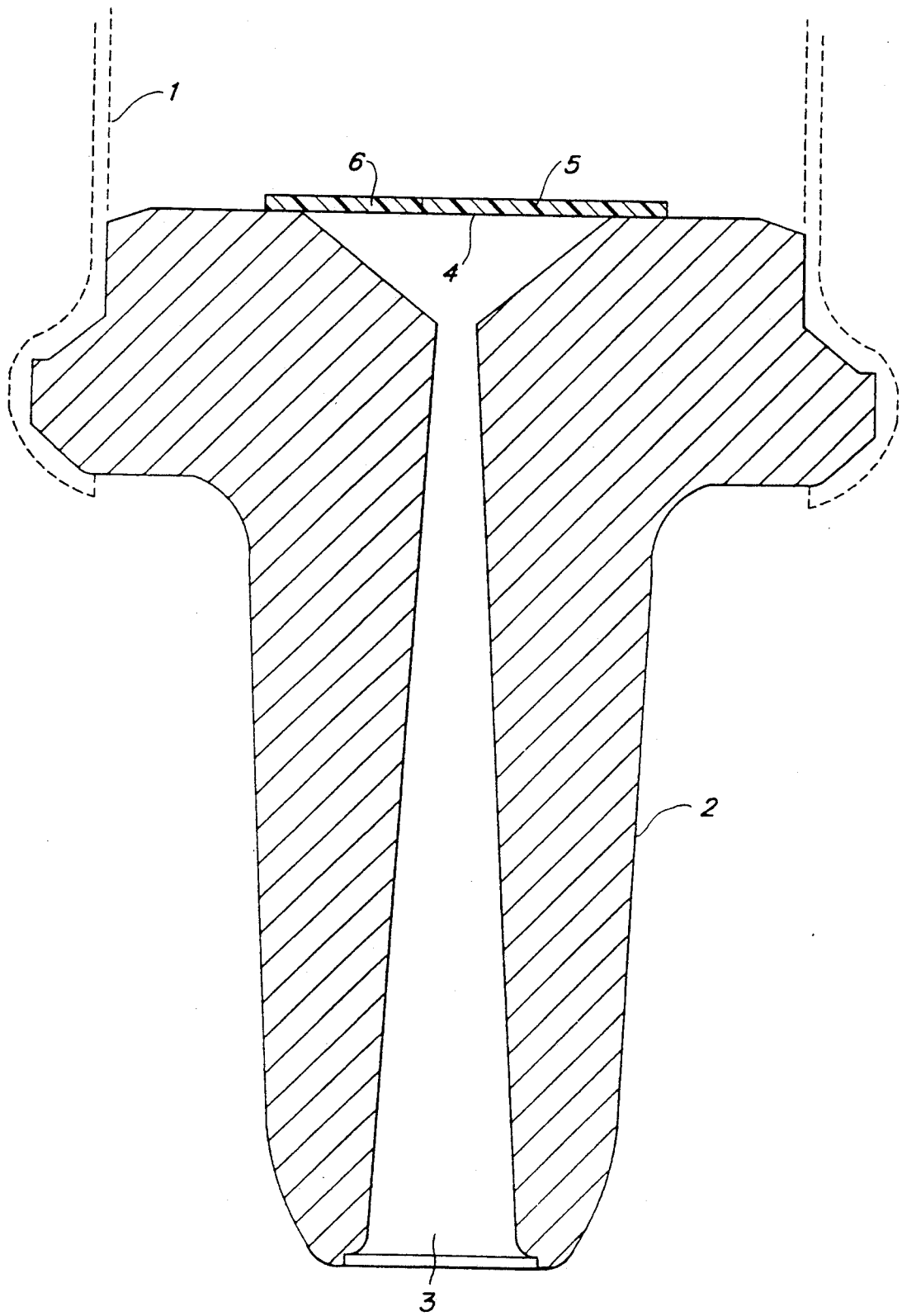
FIG. 1 is a diagrammatic cross-section of the tip and adjacent portions of a deformable container according to the invention.
Figure 2:
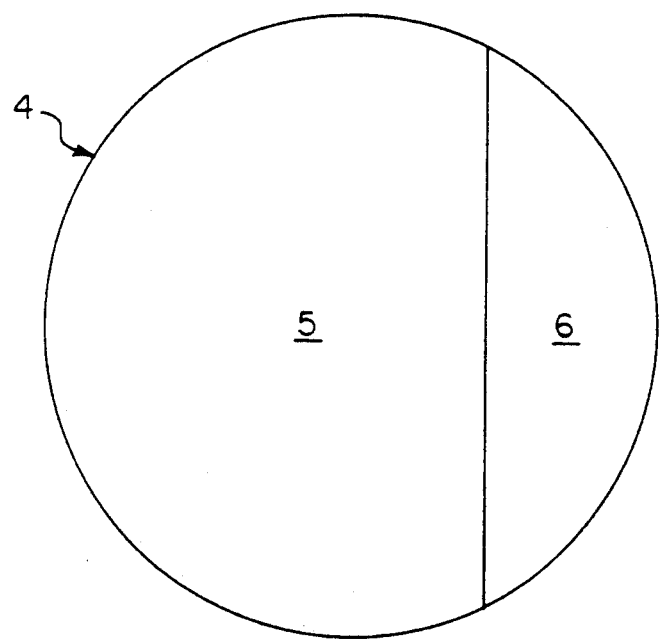
FIG. 2 is a plan view of the microporous membrane shown separate from the container.

The invention is further described with specific reference to the drawings which illustrate a preferred embodiment of the invention. In the drawings, FIG. 1 represents a partial cross-section of a dropper according to the invention. FIG. 2 represents a plan view of a composite membrane according to the invention.

In FIG. 1, a container (partially shown in dotted outline as 1) has a dropper tip 2 which terminates in an orifice 3. Disposed in the dropper tip 2 adjacent the container is a membrane 4 sealed to the surface of the dropper tip 2. The membrane 4 has a generally circular configuration conforming to the dimensions of the opening in the dropper tip 2. The membrane 4 is a composite of two components in side-by-side relationship: a liquophilic component 5 and a liquophobic component 6 sealed at their line of contact to form a unitary disc-shaped composite membrane. In use, the container is inverted, that is to say, placed with its dropper tip downwards, and squeezed. This reduces the effective volume of the container and creates a pressure differential between the inside and the outside of the container such that the liquid contained therein is expelled. The liquid is typically a drug in an aqueous solution intended for treatment of eye disorders. The drug solution wets and then passes through the liquophilic membrane into the dropper tip. As the pressure is maintained, the liquid emerges from the dropper tip orifice and begins to form a pendant drop. When used for administering ocular medicine, it is intended that this drop fall into the eye of the patient. As the drop reaches critical size, it breaks away from the dropper tip orifice and falls into the eye. When the squeezing pressure on the container is removed, a differential pressure is created between the outside of the container and the inside, as the elastic walls of the container attempt to return to their original shape. This differential pressure causes the liquid remaining in the dropper tip to be drawn back towards the inside of the container. In doing so, the liquid must pass through the liquophilic component of the membrane. The dropper tip is designed so that substantially all, if not all, of the liquid remaining after the drop is dispensed is drawn back into the container. As the retreating liquid/air interface in the dropper tip reaches the liquophilic membrane, flow through the liquophilic membrane halts. This is because significantly higher pressure than is available from recovery of the elastically deformed walls of the container, which reverses the pressure differential referred to above, is required to drive air through the wetted liquophilic membrane. Incoming air, however, is necessary to compensate for the volume of the drug dispensed. This can enter the container through the adjacent liquophobic membrane. Thus, sufficient air will enter the container via the liquophobic membrane to equalize the pressure inside and out.

In the event that the liquid in the dropper tip has become contaminated, for example, by contact with bacteria from the patient's optical fluids, the bacterial component is filtered by the liquophilic component as the rest of the liquid is drawn back into the container. Thus, liquid and air re-entering the container from the dropper tip area are filtered free of bacterial contamination.

Since the internal volume and shape of the dropper tip are selected to minimize the possibility of any retained liquid, any bacteria present and trapped on the liquophilic and liquophobic membrane components are thus exposed to the air. Such exposure may inhibit growth such that subsequent drops dispensed from the container will be either free or substantially free of contaminants previously entrained in the dropper tip. Thus, the tip will be returned substantially to its pre-contamination state with each cycle of use. If contamination is likely to have occurred and it is imperative that no amount of bacteria be returned to the eye, then the first drop or drops of drug may be discarded so as to purge the tip. Experiments in which the dropper has been seeded with known levels of bacteria suggest that this procedure is effective.

EXPERIMENTAL DATA

To test the concept, two dropper bottles and tips were constructed using a 0.2 μm rated Biodyne® nylon 66 membrane as the liquophilic segment, and 0.02 μm rated polytetrafluoroethylene membrane as the liquophobic segment. The membranes were first bonded together along their midlines using a Branson ultrasonic welder with a gold booster and a flat 2"×2" welding horn. An approximately 1 to 3 mm overlap was formed at the weld line. The dropper tips were modified by filling the excess space between the membrane and the tip with an epoxy compound, resulting in a volume of approximately 0.1 cm$^3$. Discs were then cut from the resulting composite strip and ultrasonically welded at their perimeters to the base of the dropper tips. In these tips approximately 60% of the total membrane area was occupied by the liquophilic membrane.

The tips were then aseptically inserted into dropper bottles containing an ophthalmic drug timolol maleate, but with no preservatives included.

A solution containing approximately 1×10$^5$ per milliliter of *p. aeuriginosa* was prepared. Bottle 1 was oriented tip upright, squeezed, and held. Then, an aliquot of 100 μl of the *p. aeuriginosa* solution was injected into the opening of the dropper tip using a microsyringe. The pressure on the bottle was then released, and the 100 μl aliquot was observed to draw back into the bottle. The second bottle, bottle C, did not have any bacteria solution injected and was kept as a control.

Ten minutes after the inoculation of bottle 1, a sequence of 4 drops of timolol maleate was squeezed out and each drop directed to fall into a quadrant of an agar plate (Q1 to Q4). Each drop was then spread by streaking across the quadrant with a sterile loop. One day later, the same procedure was repeated with another agar plate. This repetitive sampling was continued for 14 days. In parallel, the control bottle, bottle C, was sampled in the identical manner.

The data for the inoculated bottle, bottle 1, is shown below:

| DAY | COLONIES/QUADRANT | | | |
| --- | --- | --- | --- | --- |
| | Q1 | Q2 | Q3 | Q4 |
| 10 min | 128 | 90 | 65 | 51 |
| 1st | 0 | 0 | 0 | 0 |
| 2nd | 0 | 0 | 0 | 0 |
| 3rd | 0 | 120[a] | 0 | 0 |
| 4th to 14th | 0 | 0 | 0 | 0 |

[a]Note: colonies seen were not *p. aeruginosa*.

The control bottle, bottle C, had zero counts for all days in all quadrants.

In this experiment, the 100 μl inoculation was observed to be drawn back into the bottle. Thus, the bacteria in the aliquot was presented to the composite membrane at the base of the dropper tip. Lack of *p. aeuriginosa* growth in the samples from days 1 to 14 demonstrates that none of the bacterial challenge reached the contents of the bottle.

The data from the 4 drop sequence taken 10 minutes after inoculation is a confirmation that *p. aeuriginosa* bacteria was present in the dropper tip and, in addition, that it would not flourish or could be purged by the removal of several drops.

In the discussion of the preferred embodiment illustrated in the drawings, a device adapted to dispense ocular medicine was taken as the paradigm. It is to be understood, however, that the device of the invention could be used for other purposes in which it is convenient to dispense the medicine in the form of drops such as, for example, medicine for the ears or the nose. In general, the medicine will be made up in an aqueous or saline solution; thus the terms liquophilic and liquophobic will most conveniently imply hydrophilic and hydrophobic, respectively. It is understood, however, that occasionally medicines are made up in a light oil and thus the broadest interpretation of liquophobic and liquophilic must embrace the use of such liquids as media for the application of the medicine.

The body of the container is provided with means for temporarily reducing the volume of the container. Typically, this will be by providing that at least part of the walls of the container are elastically deformable. Thus squeezing the container will temporarily reduce its volume. Alternative means such as a movable plunger or an inflatable insert in the container could be devised but are not generally preferred over the simplicity of the squeezable container.

Figure 3:
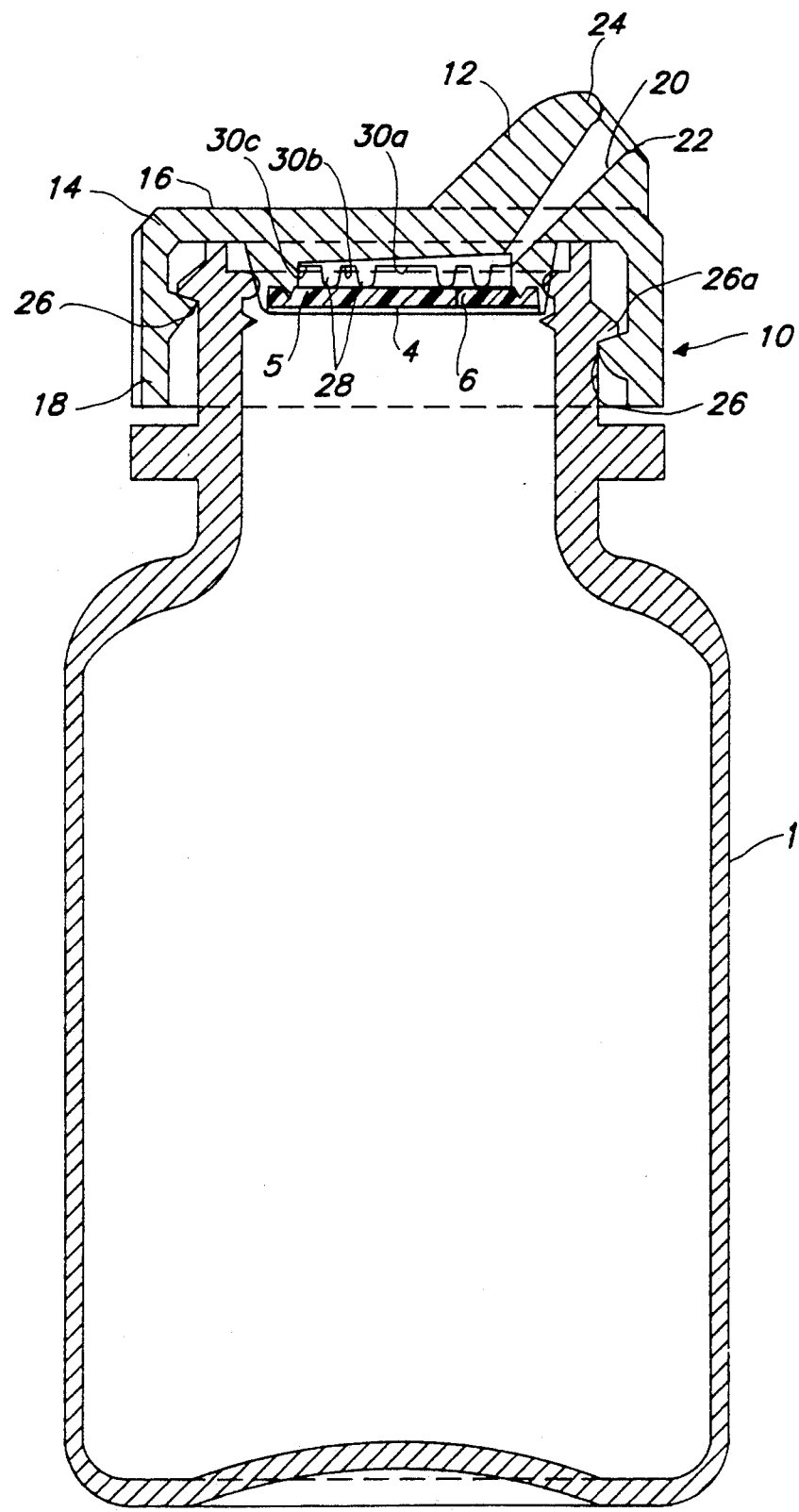
FIG. 3 is a sectional view of a container and a preferred embodiment of a liquid dispensing cap attached thereto according to the present invention.
Figure 5:
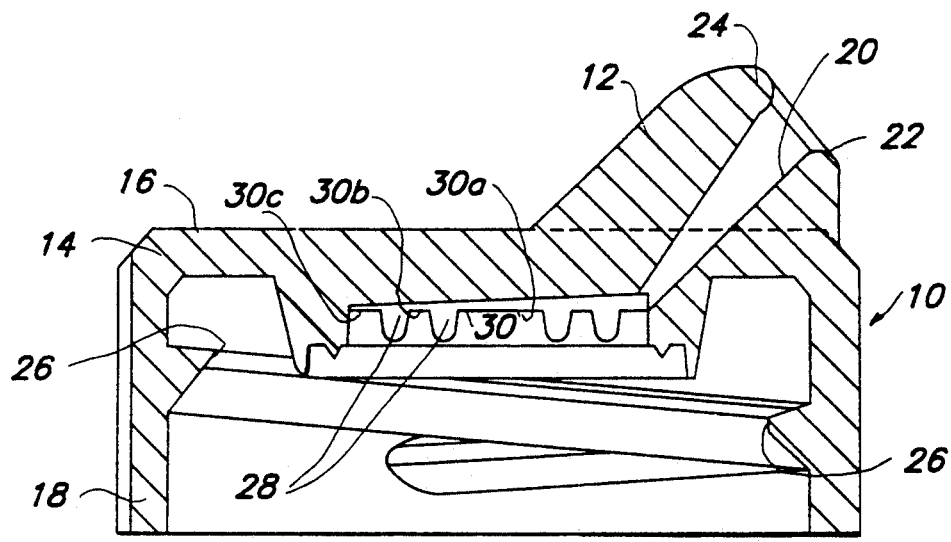
FIG. 5 is a sectional view of a preferred embodiment of the cap according to the present invention taken along lines 5—5 of FIG. 4.
Figure 4:
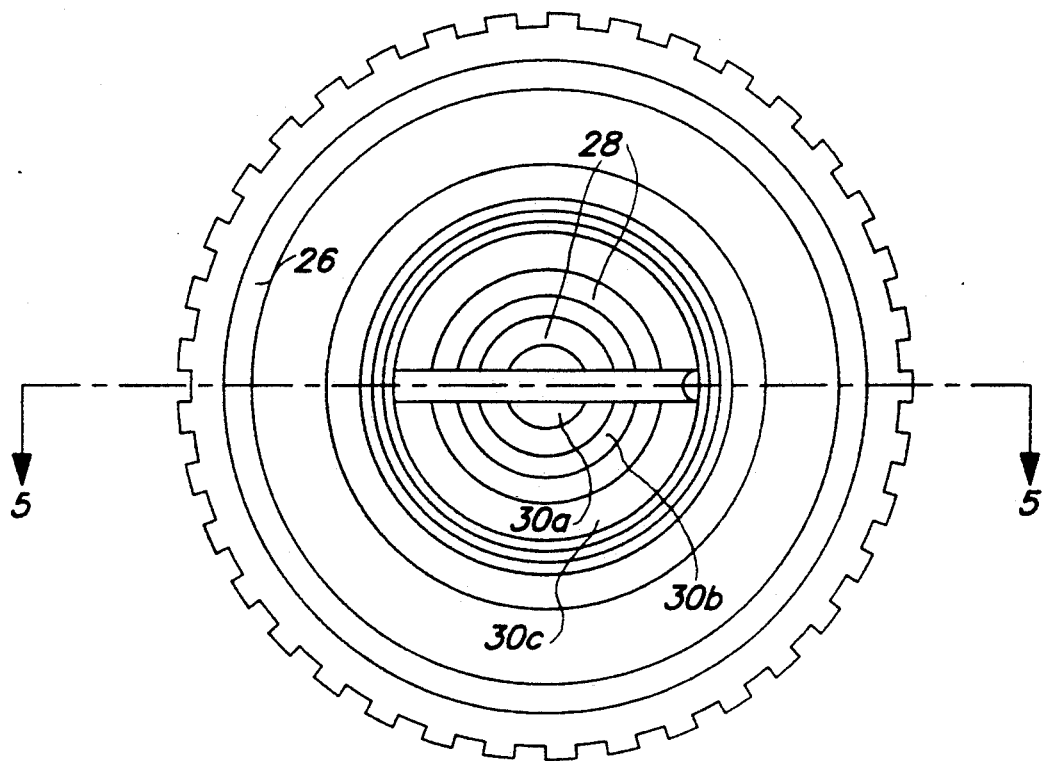
FIG. 4 is a plan view illustrating functional and ornamental features of the underside of the cap shown in FIG. 3.
Figure 8:
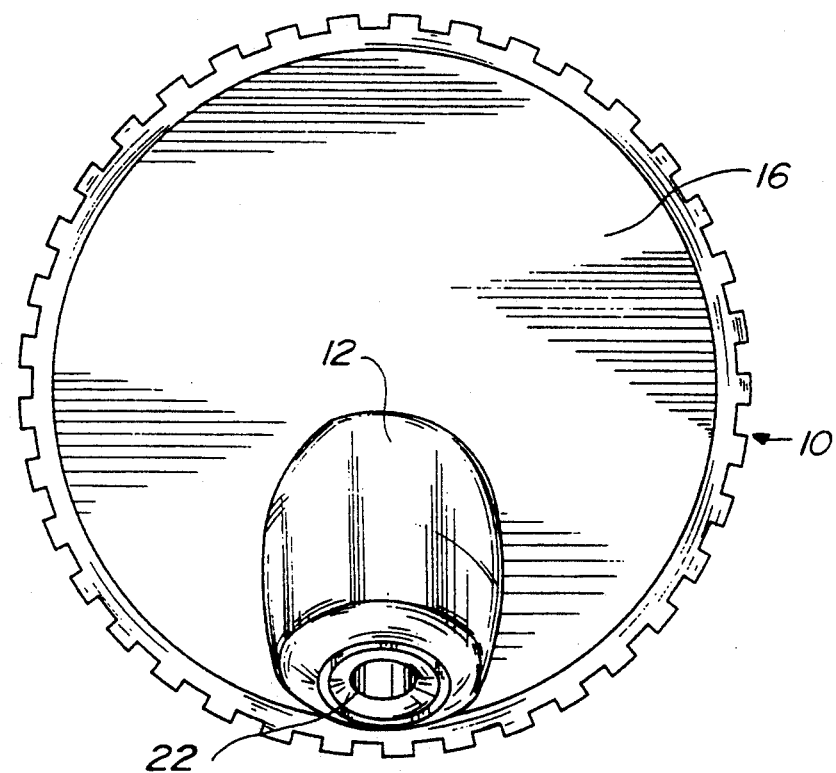
FIG. 8 is a top plan view illustrating ornamental features of the dispenser cap according to the present invention.
Figure 7:
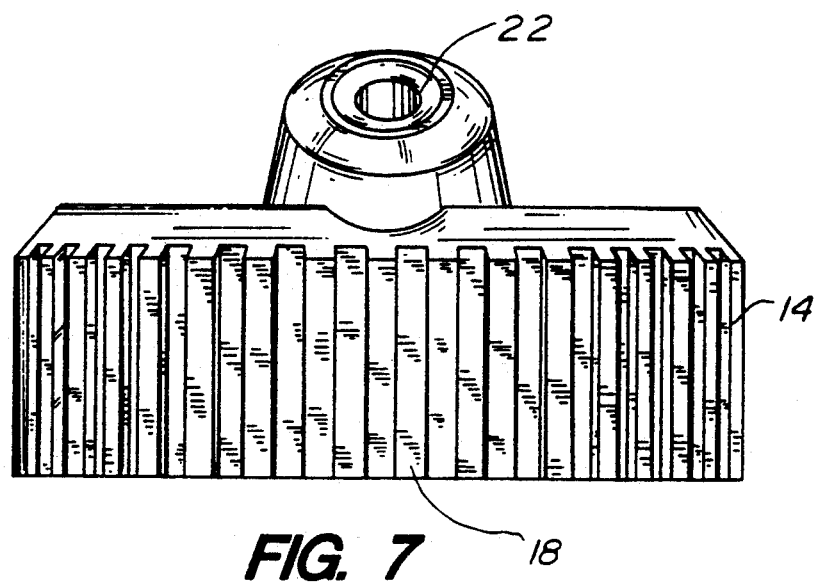
FIG. 7 is a front view showing ornamental features of the cap according to the present invention.

A preferred embodiment of a liquid dispensing cap according to the present invention is shown in FIGS. 3 to 8. FIGS. 3 to 5 illustrate structural features of the dispensing cap while FIGS. 6 to 8 illustrate ornamental features of the cap. The preferred embodiment of the cap, generally designated by reference number 10, is shown in an assembled state in FIG. 3 and removed from the container in FIG. 5. The cap is composed of a dropper or dispenser tip 12 which projects from a base 14. The latter is formed from a top portion 16 and a skirt portion 18. The dropper tip 12 is provided with a passageway 20 which provides fluid communication between the inside of the cap and an aperture or orifice 22 formed at the distal end 24 of the dropper tip. While any means of attaching the cap to the container 1 may be employed, simple threading provided on a portion of the cap, such as the skirt, and commensurate threading on the container is quite effective in attaching the base of the cap to the container. FIG. 3 shows threads 26 and engaging threads 26a on the cap and container, respectively. Although the threading is shown in FIGS. 3 and 5 on the interior of the cap, such threading may also be placed on the exterior portion of the skirt and threaded into the neck of a container which is provided with commensurately configured threading on the interior surface of the neck.

As shown in FIG. 3 and 5, rather than being coaxial as a typical dropper dispenser in which the dropper tip is located centrally with respect to the longitudinal axis of the container, the cap 10 is provided with a dispenser tip 12 located off center with respect to the longitudinal axis of the container and the cap. The preferred position of the dropper tip is at or proximate a side of the base (skirt portion 18) as shown in FIGS. 3 and 5. As shown in these figures, the surface of a side of the dropper tip closest to the side of the cap is almost coextensive with or tangent to a portion of the skirt of the base.

The orientation of the passageway also differs from a conventional dispenser in that the axis of the passageway is not parallel to the longitudinal axis of the cap or the container but rather ranges from being slightly greater than a position parallel to the longitudinal axis of the cap (0°) to defining an angle with the longitudinal axis of the cap of almost 90°. Preferably, the angle formed between the longitudinal axis of the cap and the axis of the passageway is about 30° to about 60°, most preferably about 40° to about 50°. The angle shown in FIGS. 3 and 5 is about 50°. This orientation of the dropper tip on the cap, when a cap is attached to a conventional container, provides the best range of motion and most comfortable position for a user to hold the dispenser when administering a liquid to the user's eye.

FIGS. 3 and 5 show a rim formed at the distal end 24 of the dispenser tip. This rim defines a plane at the distal end of the dispenser tip, which plane forms an angle with respect to the axis of the passageway of 90° ± about 45°. The angle shown in FIGS. 3 and 5 is about 90°.

Semicircular ribs 28 are provided on the interior of the dispenser cap to provide support at strategic positions for a membrane 4. As shown best in FIG. 4, the discontinuity in the structure of the ribs permits fluid flow from one "sub-chamber" defined by the membrane 4, ribs 28 and the centrally located interior surface of the underside of the cap 30. The centrally located surface 30 is divided by the ribs into concentric regions 30a, 30b and 30c. To provide directed liquid flow to the passageway, a channel or trough 32 extends from beneath (when in an inverted position) and coextensive with the membrane 4 and also the region of discontinuity of the ribs from one edge of the membrane to the opposite side of the membrane. The trough or recessed area 32 descends (when the cap is in an inverted position) as it approaches the passageway, with which it communicates.

When a composite membrane is employed with this embodiment of the dispenser cap, the liquophobic or hydrophobic component 6 is arranged so that it is closest to the passageway of the dispenser tip. Accordingly, the liquophilic or hydrophilic component 5 is arranged to be closest to the side of the cap opposite the dispenser tip.

We claim:

1. A cap for dispensing liquids from a container comprising:
   a base portion having a skirt portion;
   means to attach said portion to a container;
   an off-center dispenser tip projecting from said base portion and having a side nearest said skirt portion substantially tangent thereto, said dispenser tip also having a passageway for ingress of air and egress of liquid, said passageway extending between an orifice at the distal end of said dispenser tip and the interior underside of said cap, the axis of said passageway forming an angle of no greater than 90° with the longitudinal axis of said base; and
   a microporous composite membrane having pores of a size to resist passage of contaminants and formed of a liquophilic component which permits passage of drops of a liquid and a liquophobic component which resists passage of such liquid but permits passage therethrough of air, the surface area and pore size of said liquophilic component being so selected as to meter liquid being dispensed in drop form and avoid a stream of liquid from emerging from the dispenser tip during normal use, said micorporous composite membrane so disposed and arranged within said cap adjacent said passageway such that said passageway communicates with both the liquophobic and liquophilic components.

2. A cap according to claim 1 wherein said angle is about 30° to about 60°.

3. A cap according to claim 1 wherein said angle is about 40° to about 50°.

4. A cap according to claim 1 wherein said base portion has a skirt portion and said side of said dispenser tip nearest said skirt portion is parallel to a skirt portion of said cap.

5. A cap according to claim 4 wherein said dispenser tip is proximate a side of said base portion.

6. A cap according to claim 1, wherein the distal end of the dispenser tip has a rim which defines a plane which forms an angle in the range of 90° ± about 45° with respect to the axis of said passageway.

7. A cap according to claim 1 wherein the distal end of the dispenser tip defines a plane which is substantially perpendicular to the axis of the dispenser tip passageway.

8. A cap according to claim 1 wherein the pore size of the liquophilic component of the membrane is from about 0.04 to about 0.65 μm.

9. A cap according to calm 1 wherein the pore size of the liquophobic component of the membrane is from about 0.01 to about 0.45 μm.

10. A cap according to claim 1 wherein the liquophilic component comprises from about 50 to about 70% of the surface area of the membrane.

11. A cap according to claim 1 wherein the volume between the composite membrane and the dropper tip orifice is from about 0.001 to about 0.15 cm$^3$.

12. A cap according to claim 1 wherein the liquophobic component has a critical wetting surface tension of less than 35 dynes/cm.

13. A cap according to claim 12 wherein the liquophilic component of the composite membrane has a critical wetting surface tension of at least 72 dynes/cm.

14. A cap according to claim 1 wherein the liquophilic component is made from a surface-modified microporous nylon polymer membrane.

15. A cap according to claim 1 wherein the liquophobic component is made from a surface-modified microporous polyvinylidene fluoride membrane.

16. A cap according to claim 1 wherein the microporous composite membrane is arranged transverse the passageway.

17. A cap according to claim 1 wherein the liquophilic component has a surface area of from about 20 mm$^2$ to about 90 mm$^2$.

18. A cap according to claim 1 wherein said composite microporous membrane has pore sizes less than 0.45 μm, said membrane comprises a hydrophilic component and a hydrophobic component, said hydrophilic component providing from about 60 to about 70% of the surface area of the composite membrane.

19. A cap according to claim 1 wherein a composite microporous membrane has first and second components bonded together in side-by-side relationship, the first component having a surface area of from about 40 mm$^2$ to about 50 mm$^2$, an average pore size of from about 0.15 to about 0.25 μm, and a CWST of at least about 72 dynes/cm and being made from a surface-modified polyamide; and the second component being made from a polyamide that has been surface-modified to produce a CWST of less than about 35 dynes/cm and having an average pore size of from about 0.1 to about 0.2 μm.

20. A cap according to claim 1 wherein the volume between the orifice of the dispenser tip and the surface of the composite membrane closest to the tip is from about 0.05 to about 0.1 cm$^3$.

21. A device according to claim 1 wherein said liquophilic component is a surface-modified microporous nylon membrane and said liquophobic component is a surface-modified microporous polyvinylidene fluoride membrane.

22. A device according to claim 1 wherein said liquophilic component comprises a surface-modified polyamide having a CWST of at least about 50 dynes/cm and said liquophobic component comprises a surface-modified polyamide having a CWST of less than about 35 dynes/cm.

23. A device according to claim 22 wherein the CWST of said liquophilic component is at least about 72 dynes/cm and said liquophobic component is less than about 29 dynes/cm.

24. A device according to claim 1 wherein said orifice comprises a single orifice.

25. A device according to claim 1 wherein said liquophilic and liquophobic components are arranged in juxtaposed relationship.

26. A device according to claim 1 wherein said liquophobic component and said liquophilic components are arranged in juxtaposed relationship and said microporous composite membrane is arranged in said cap with the liquophilic portion adjacent the side of said cap opposite that at which said dispenser tip is located.

27. A device for dispensing a liquid comprising:
   (a) a container,
   (b) means for reducing the volume of the container;
   (c) a cap for dispensing liquid from said container including:
      (1) a base portion having a skirt portion attached to said container, and
      (2) an off-center dispenser tip projecting from said base portion and having a side nearest said skirt portion substantially tangent thereto, said dispenser tip also having a passageway for ingress of air and egress of liquid, said passageway extending between an orifice at the outer end of said dispenser tip and the interior of said cap in fluid communication with said container, the axis of said passageway forming an angle no greater than 90° with the longitudinal axis of said base portion;

a microporous composite membrane having pores of a size to resist passage of contaminants and formed of a liquophilic component which permits passage of drops of a liquid and a liquophobic component which resists passage of such liquid but permits passage therethrough of air, the surface area and pore size of said liquophilic component being so selected as to meter liquid being dispensed in drop form and avoid a stream of liquid from emerging from the dispenser tip during normal use, said micorporous composite membrane so disposed and arranged within said cap adjacent said passageway such that said passageway communicates with both the liquophobic and liquophilic components.

28. A cap according to claim 27 wherein said angle is about 30° to about 60°.

29. A cap according to claim 27 wherein said angle is about 40° to about 50°.

30. A cap according to claim 27 wherein said base portion has a skirt portion is parallel to a skirt portion of said cap.

31. A cap according to claim 30 wherein said dispenser tip is proximate a side of said base portion.

32. A cap according to claim 27, wherein the distal end of the dispenser tip defines a plane which forms an angle with respect to the longitudinal axis of the cap of about 90° to no more than about 180°.

33. A cap according to claim 27 wherein the distal end of the dispenser tip defines a plane which is substantially perpendicular to the axis of the dispenser tip passageway.

34. A cap according to claim 27 wherein the pore size of the liquophilic component of the membrane is from about 0.04 to about 0.65 $\mu$m.

35. A cap according to claim 27 wherein the pore size of the liquophobic component of the membrane is from about 0.01 to about 0.45 $\mu$m.

36. A cap according to claim 27 wherein the liquophilic component comprises from about 50 to about 70% of the surface area of the membrane.

37. A cap according to claim 27 wherein the volume between the composite membrane and the dispenser tip orifice is from about 0.001 to about 0.15 cm$^3$.

38. A cap according to claim 27 wherein the liquophobic component has a critical wetting surface tension of less than 35 dynes/cm.

39. A cap according to claim 27 wherein the liquophilic component of the composite membrane has a critical wetting surface tension of at least 72 dynes/cm.

40. A cap according to claim 27 wherein the liquophilic component is made from a surface-modified microporous nylon polymer membrane.

41. A cap according to claim 27 wherein the liquophobic component is made from a surface-modified microporous polyvinylidene fluoride membrane.

42. A cap according to claim 27 wherein the microporous composite membrane is arranged transverse the passageway.

43. A cap according to claim 27 wherein the liquophilic component has a surface area of from about 20 mm$^2$ to about 90 mm$^2$.

44. A cap according to claim 27 wherein said composite microporous membrane has pore sizes less than 0.45 $\mu$m, said membrane comprises a hydrophilic component and a hydrophobic component, said hydrophilic component providing from about 60 to about 70% of the surface area of the composite membrane.

45. A cap according to claim 27 wherein a composite microporous membrane has first and second components bonded together in side-by-side relationship, the first component having a surface area of from about 40 mm$^2$ to about 50 mm$^2$, an average pore size of from about 0.15 to about 0.25 $\mu$m, and a CWST of at least about 72 dynes/cm and being made from a surface-modified polyamide; and the second component being made from a polyamide that has been surface-modified to produce a CWST of less than about 35 dynes/cm and having an average pore size of from about 0.1 to about 0.2 $\mu$m.

46. A cap according to claim 27 wherein the volume between the orifice of the dispenser by and the surface of the composite membrane closest to the tip is from about 0.05 to about 0.1 cm$^3$.

47. A device according to claim 27 wherein said liquophilic component is a surface-modified microporous nylon membrane and said liquophobic component is a surface-modified microporous polyvinylidene fluoride membrane.

48. A device according to claim 27 wherein said liquophilic component comprises a surface-modified polyamide having a CWST of at least about 50 dynes/cm and said liquophobic component comprises a surface-modified polyamide having a CWST of less than about 35 dynes/cm.

49. A device according to claim 27 wherein the CWST of said liquophilic component is at least about 72 dynes/cm and said liquophobic component is less than about 29 dynes/cm.

50. A device according to claim 27 wherein said orifice comprises a single orifice.

51. A device according to claim 27 wherein said liquophilic and liquophobic components are arranged in juxtaposed relationship.

52. A device according to claim 27 wherein said liquophobic component and said liquophilic components are arranged in juxtaposed relationship and said microporous composite membrane is arranged in said cap with the liquophilic portion adjacent the side of said cap opposite that at which said dispenser tip is located.

53. A device according to claim 1 wherein said liquophobic component and said liquophilic components are arranged in juxtaposed relationship and said microporous composite membrane is arranged in said cap with the liquophilic portion adjacent the side of said cap opposite that at which said dispenser tip is located.

* * * * *

UNITED STATES PATENT AND TRADEMARK OFFICE
CERTIFICATE OF CORRECTION

PATENT NO. : 5,265,770
DATED : November 30, 1993
INVENTOR(S) : Matkovich et al.

It is certified that error appears in the above-indentified patent and that said Letters Patent is hereby corrected as shown below:

In item no. [57], Abstract, line 7, after "90" insert "°". (Title Page)

Claim 46, column 18, line 29, change "by" to --tip--.

Signed and Sealed this

Seventh Day of June, 1994

Attest:

BRUCE LEHMAN

*Attesting Officer*  *Commissioner of Patents and Trademarks*